US012336707B2

(12) United States Patent
Ding

(10) Patent No.: US 12,336,707 B2
(45) Date of Patent: Jun. 24, 2025

(54) CARTRIDGE ASSEMBLY AND SURGICAL STAPLER

(71) Applicant: TOUCHSTONE INTERNATIONAL MEDICAL SCIENCE CO., LTD., Suzhou (CN)

(72) Inventor: Shuicheng Ding, Suzhou (CN)

(73) Assignee: TOUCHSTONE INTERNATIONAL MEDICAL SCIENCE CO., LTD., Suzhou (CN)

(*) Notice: Subject to any disclaimer, the term of this patent is extended or adjusted under 35 U.S.C. 154(b) by 0 days.

(21) Appl. No.: 18/736,309

(22) Filed: Jun. 6, 2024

(65) Prior Publication Data

US 2024/0315694 A1 Sep. 26, 2024

Related U.S. Application Data

(63) Continuation of application No. PCT/CN2022/138533, filed on Dec. 13, 2022.

(30) Foreign Application Priority Data

Dec. 17, 2021 (CN) .......................... 202123200263.1

(51) Int. Cl.
*A61B 17/072* (2006.01)
*A61B 17/068* (2006.01)
*A61B 17/115* (2006.01)

(52) U.S. Cl.
CPC .......... *A61B 17/072* (2013.01); *A61B 17/068* (2013.01); *A61B 17/07207* (2013.01); *A61B 2017/07214* (2013.01); *A61B 2017/07271* (2013.01); *A61B 2017/07285* (2013.01); *A61B 17/115* (2013.01)

(58) Field of Classification Search
CPC . A61B 17/068; A61B 17/0644; A61B 17/072; A61B 17/07207; A61B 17/115; A61B 2017/07214; A61B 2017/07271; A61B 2017/07285
USPC ..... 227/19, 175.1, 176.1, 180.1; 606/1, 139, 606/219
See application file for complete search history.

(56) References Cited

U.S. PATENT DOCUMENTS

| 4,011,699 A * | 3/1977 | Mickelson ............ B66C 23/705 52/115 |
| 8,070,036 B1 * | 12/2011 | Knodel ............ A61B 17/07207 227/175.1 |
| 8,261,958 B1 * | 9/2012 | Knodel ............ A61B 17/07207 227/176.1 |

(Continued)

*Primary Examiner* — Scott A Smith
(74) *Attorney, Agent, or Firm* — Westbridge IP LLC

(57) ABSTRACT

A cartridge assembly and a surgical stapler are provided. The cartridge assembly includes: a cartridge including a cartridge surface provided with a plurality of staple cavities, staple mating portions provided on proximal sides of the staple cavities; a plurality of staples located in the staple cavities; an actuation member configured to drive the staples and the staple mating portions to rotate in a first direction when the actuation member moves from a proximal side toward a distal side of the cartridge. After each staple mating portion rotates, the second connecting portion of the corresponding staple is driven by the staple mating portion to move away from the cartridge and then separates from the staple cavity, so the staples can be more easily separated with the cartridge after being closed.

11 Claims, 4 Drawing Sheets

(56) References Cited

U.S. PATENT DOCUMENTS

| | | | |
|---|---|---|---|
| 9,655,613 B2 * | 5/2017 | Schaller | A61B 17/07207 |
| 10,548,599 B2 * | 2/2020 | Marczyk | A61B 17/0644 |
| 11,490,893 B2 * | 11/2022 | Marczyk | A61B 17/105 |
| 2014/0263546 A1 * | 9/2014 | Aranyi | A61B 17/07207 |
| | | | 227/175.2 |
| 2014/0263557 A1 * | 9/2014 | Schaller | A61B 17/07207 |
| | | | 227/176.1 |
| 2015/0173748 A1 * | 6/2015 | Marczyk | A61B 17/0644 |
| | | | 227/177.1 |

* cited by examiner

CARTRIDGE ASSEMBLY AND SURGICAL STAPLER

CROSS-REFERENCE TO RELATED APPLICATIONS

This application is a continuation of International Application No. PCT/CN2022/138533, filed on Dec. 13, 2022, which claims priority to Chinese Patent Application No. CN 202123200263.1, filed on Dec. 17, 2021, the entire contents of which are incorporated herein by reference.

TECHNICAL FIELD

The present disclosure relates to technology of surgical instruments, more particularly, to a cartridge assembly and a surgical stapler.

BACKGROUND

In the prior art, a surgical stapler generally includes an instrument platform, a movable handle movably connected to the instrument platform, and a head assembly mounted on the instrument platform. The head assembly can pass through a small incision in the body using a trocar to access the surgical site for surgery. The head assembly includes a cartridge assembly and an anvil arranged relative to the cartridge assembly. Many staples are mounted in the cartridge assembly. During the firing process of the stapler, the staples are forced toward the anvil by an actuation member, then the staples are closed and formed at the anvil to suture the tissues. However, after the stapler is fired, the staples may not be completely separated from the cartridge, so the surgical effect is affected.

SUMMARY

To solve the problems in the prior art, the present disclosure aims to provide a cartridge assembly and a surgical stapler, so the staples can be more easily separated with the cartridge after being closed.

In the present disclosure, a cartridge assembly used for a surgical stapler is provided, including: a cartridge including a cartridge surface, wherein the cartridge surface is provided with a plurality of staple cavities, staple mating portions are provided on proximal sides of the staple cavities, each staple mating portion includes a first connecting portion, and the staple mating portion is configured to be rotatably connected to a lower side of the cartridge surface through the first connecting portion; a plurality of staples configured to be located in the staple cavities, wherein each staple includes a second connecting portion, and the staple is configured to be rotatably connected to an inner wall of the staple cavity through the second connecting portion; wherein each staple mating portion is on a proximal side of the second connecting portion of a corresponding staple; an actuation member configured to drive the staples and the staple mating portions to rotate in a first direction when the actuation member moves from a proximal side toward a distal side of the cartridge; wherein after each staple mating portion rotates, the second connecting portion of the corresponding staple is driven by the staple mating portion to move away from the cartridge and be separated from the staple cavity.

In some embodiments, a first mating portion is provided on an inner wall of at least one side of the staple cavity, the second connecting portion of the staple is provided with a second mating portion, the second mating portion and the first mating portion are configured to form embedded cooperation, the second mating portion is rotatable and separable relative to the first mating portion, and the staple mating portion is on a proximal side of the first mating portion.

In some embodiments, a receiving space is configured to be formed between the proximal side of the first mating portion and a distal surface of the staple mating portion; wherein after the staple mating portion is driven by the actuation member to rotate in the first direction, the staple mating portion at least partially enters the receiving space.

In some embodiments, the staple mating portion is configured to be at least partially under the second connecting portion after the staple mating portion is rotated in the first direction.

In some embodiments, a lowest point of the staple is lower than that of the staple mating portion in a height direction; wherein, when the actuation member moves distally, the actuation member first drives the staple to rotate in the first direction, and when the actuation member continues to move distally after the staple is rotated by a first angle, the actuation member drives the staple mating portion to rotate in the first direction.

In some embodiments, the staple mating portion is configured to be integrally formed with the cartridge, and the staple mating portion is configured to be connected with the inner wall of the staple cavity through weak link at a position of the first connecting portion.

In some embodiments, a distal surface of the staple mating portion is an inclined surface, and the distal surface of the staple mating portion is configured to abut the staple in an initial state.

In some embodiments, after the actuation member drives the staple mating portion to rotate in the first direction, the staple mating portion remains connected with the cartridge.

In some embodiments, a proximal surface of the staple mating portion is a vertical surface.

In some embodiments, an upper surface of the staple mating portion is a plane parallel to an axial direction of the stapler, and/or, an arc-shaped guiding surface is provided between a lower surface of the staple mating portion and a distal surface of the staple mating portion.

In the present disclosure, a surgical stapler including the cartridge assembly is provided.

The cartridge assembly and the surgical stapler have the following advantages.

The present disclosure provides a cartridge assembly used for a surgical stapler. During the firing process of the stapler, the actuation member drives the staples and the staple mating portions to move in a first direction. The staples can be closed and formed under the action of the anvil. After the staples are closed, the staple mating portions can assist in driving the staples to separate from the cartridge. Therefore, the situation that the staples cannot be completely separated from the cartridge is avoided, and the surgical effect is improved.

BRIEF DESCRIPTION OF THE DRAWINGS

By reading the detailed description of non-limiting embodiments with reference to the following drawings, other features, objectives, and advantages of the present disclosure will become more apparent.

DETAILED DESCRIPTION OF THE EMBODIMENTS

Figure 1:
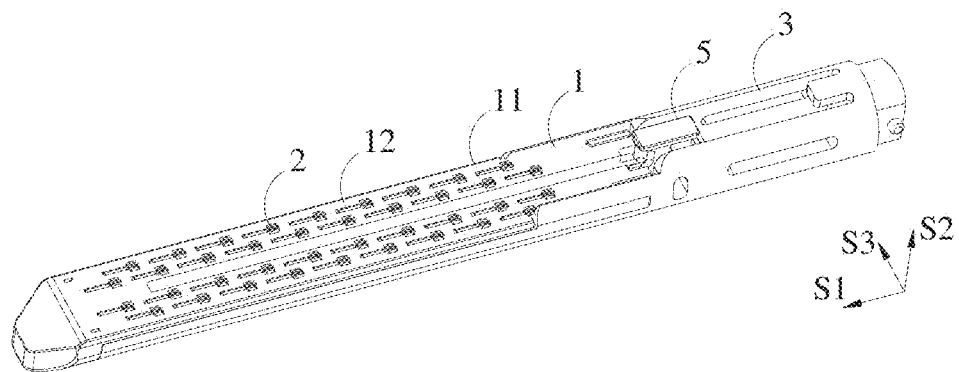
FIG. 1 is a schematic structural view of a cartridge assembly according to an embodiment of the present disclosure.

The exemplary embodiments will be more comprehensively described by combining the drawings. However, the exemplary embodiments can be implemented in multiple forms and should not be limited to the embodiments described herein. On the contrary, providing these embodiments will make the present disclosure comprehensive and complete, and will comprehensively convey the concept of the exemplary embodiments to those skilled in the art. The same reference numbers in the drawings represent the same or similar structures, so repeated descriptions of them will be omitted.

The present disclosure provides a cartridge assembly used for a surgical stapler and a surgical stapler including the same. The surgical stapler generally includes an instrument platform, a movable handle movably connected to the instrument platform, and a head assembly mounted on the instrument platform. The head assembly includes a cartridge assembly and an anvil arranged relative to the cartridge assembly. The cartridge assembly includes a plurality of staples, a cartridge for receiving the staples, and an actuation member for driving the staples. Wherein, the cartridge includes a cartridge surface, a plurality of staple cavities are provided on the cartridge surface, and staple mating portions are provided on proximal sides of the staple cavities. Each staple mating portion includes a first connecting portion, and the staple mating portion is rotatably connected to a lower side of the cartridge surface through the first connecting portion. The plurality of staples are located in the staple cavities. Each staple includes a second connecting portion and is rotatably connected to the staple cavity through the second connecting portion. The staple mating portion is located on a proximal side of the second connecting portion of the staple.

When the actuation member moves from a proximal side to a distal side of the cartridge, the actuation member drives the staples and the staple mating portions to rotate in a first direction. When the staples rotate, staple legs extend outward from the staple cavities and contact an anvil surface of the anvil, then the staples are closed and formed under the action of the anvil. The distal surfaces of the staple mating portions drive the second connecting portions of the staples to move away from the cartridge, and assist the actuation member in driving the staples to separate from the cartridge after the staples are closed, so the situation that the staple cannot be completely separated from the cartridge is avoided, and the surgical effect is improved.

The structure of the cartridge assembly of each embodiment of the present disclosure is described in detail below with reference to the accompanying drawings. It can be understood that the various embodiments are not intended to limit the scope of protection of the present disclosure.

Figure 2:
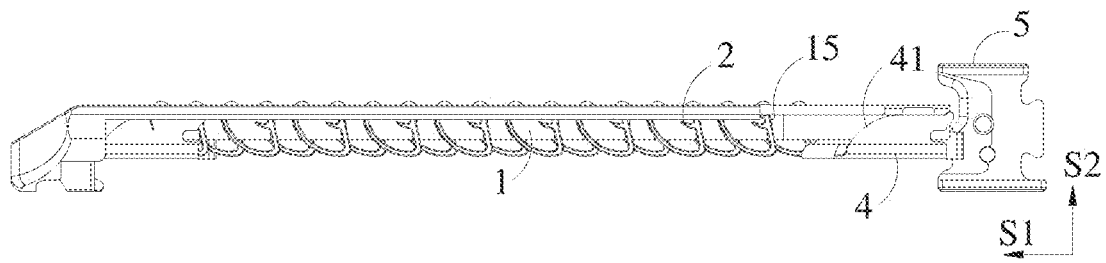
FIG. 2 is a schematic structural view of the cartridge assembly omitting a cartridge carrier and a cartridge cover according to the embodiment of the present disclosure.
Figure 4:
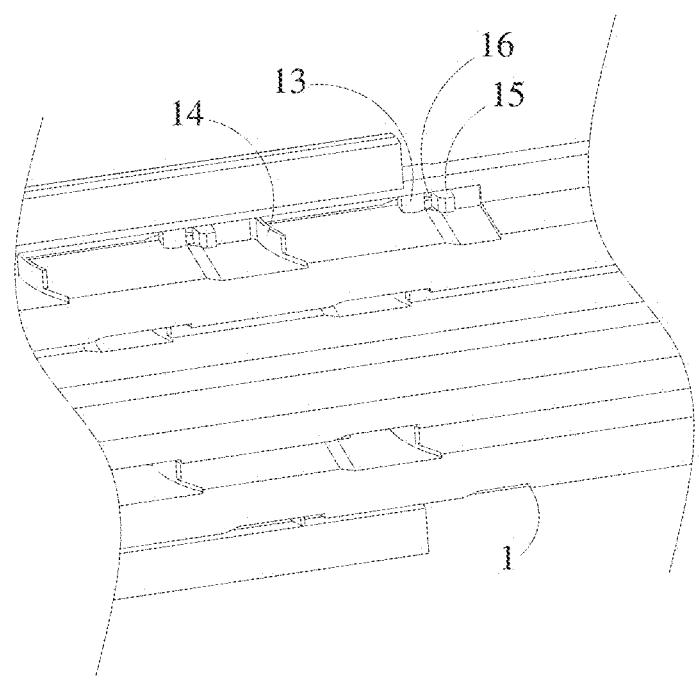
FIG. 4 is a stereogram of a cartridge according to the embodiment of the present disclosure.
Figure 5:
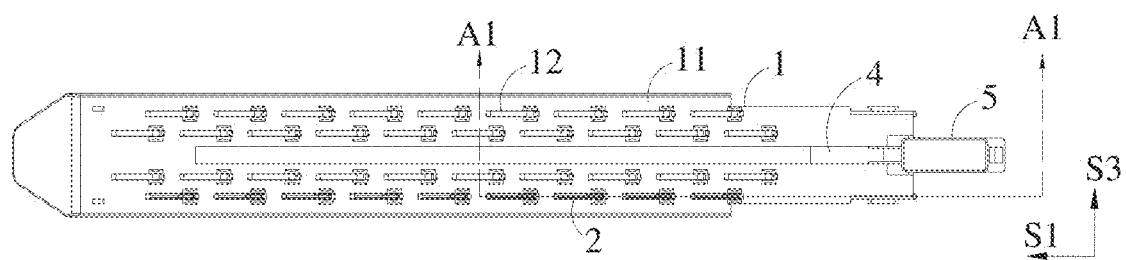
FIG. 5 is a top view of the cartridge assembly omitting the cartridge carrier and the cartridge cover according to the embodiment of the present disclosure.
Figure 6:
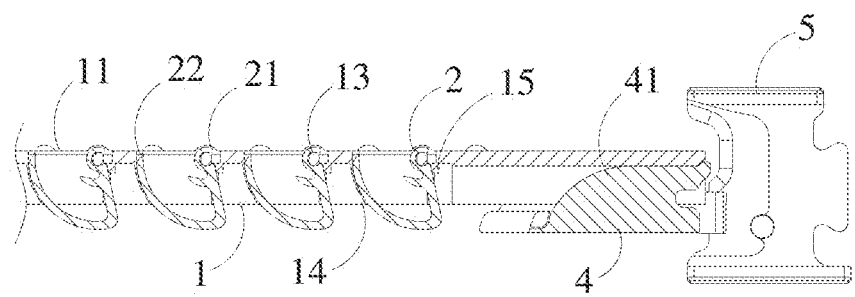
FIG. 6 is a cross-sectional view taken in A1-A1 direction in FIG. 5.

FIGS. 1 to 8 are schematic structural views of a cartridge assembly according to an embodiment of the present disclosure. As shown in FIG. 1 and FIG. 2, in this embodiment, the cartridge assembly includes a plurality of staples 2, a cartridge 1 for receiving the staples 2, and an actuation member 4 for driving the staples 2. A surface of the cartridge 1 facing the anvil is a cartridge surface 11 (in the perspective of FIG. 1, the cartridge surface 11 is an upper surface of the cartridge 1). The cartridge assembly further includes a cartridge cover (not shown) located outside the cartridge 1, a cartridge carrier 3 and a knife 5. The cartridge carrier 3 is used for receiving the cartridge 1 and the cartridge cover. The knife 5 is located on a proximal side of the actuation member 4. The cartridge 1 is provided with a plurality of staple cavities 12, the plurality of staples 2 are in the staple cavities 12. Each staple 2 includes a second connecting portion 21 and is rotatably connected to an inner wall of the staple cavity 12 through the second connecting portion 21. Staple mating portions 15 are provided on proximal sides of the staple cavities 12. Each staple mating portion 15 includes a first connecting portion 151, and the staple mating portion 15 is rotatably connected to a lower side of the cartridge surface 11 through the first connecting portion 151. The staple mating portion 15 is located on a proximal side of the second connecting portion 21 of the staple 2. In this embodiment, the staple mating portion 15 is a block connected to the lower side of the cartridge surface 11. In the embodiment, the lower side of the cartridge surface 11 refers to the side of the cartridge surface 11 away from the anvil of the stapler. In the perspective of FIG. 6, the lower side of the cartridge surface 11 is the side under the cartridge surface 11.

During the firing process of the stapler, driven by a firing bar, the knife 5 drives the actuation member 4 to move distally, and the actuation member 4 drives the staples 2 and the staple mating portions 15 to rotate in the first direction. In the perspective of FIG. 2, the first direction is clockwise direction. When the staplers 2 rotate, the staple legs 22 extend outward from the staple cavities 12 and contact the anvil surface of the anvil, then the staples are closed and formed under the action of the anvil. Distal surfaces 152 of the staple mating portions 15 drive the second connecting portions 21 of the staples 2 to move away from the cartridge 1 (in the perspective of FIG. 2, that is, the staple mating portions 15 drive the second connecting portions 21 to move upward). The staple mating portions 15 assist the actuation member 4 in driving the staples 2 to separate from the cartridge 1 after the staples 2 are closed, so the situation that the staples 2 cannot be completely separated from the cartridge 1 is avoided, and the surgical effect is improved.

In the present disclosure, the distal side and the proximal side are defined relative to the operator, the side close to the operator is the proximal side, and the side away from the operator, that is, the side close to the surgical state is the distal side. The extending direction of the axis of the stapler is the axial direction, that is, the direction from the distal side to the proximal side of the stapler, or from the proximal side to the distal side of the stapler. For example, in the perspective of FIG. 1, the distal side of the cartridge 1 is the left side, and the proximal side of the cartridge 1 is the right side. Direction S1 is the direction from the proximal side to the distal side of the stapler. The direction S1 or the direction opposite to the direction S1 is defined as the axial direction of the stapler. Direction S2 in FIG. 1 is defined as the height direction, that is, the longitudinal direction. Direction S3 in FIG. 1 is defined as the width direction, that is, the transverse direction.

As shown in FIGS. 3 to 8, in this embodiment, an inner wall of at least one side of the staple cavity 12 is provided with the first mating portion, and the second connecting portion 21 of the staple 2 is provided with a second mating portion. The second mating portion and the first mating portion form embedded cooperation. The second mating portion is rotatable and separable relative to the first mating portion. In this embodiment, the first mating portion is a rotating shaft 13, and the second mating portion is a mounting hole 211 having an opening. The second connecting portion 21 is rotatably jacketed on the rotating shaft 13 through the mounting hole 211. After the staple 2 is closed, the opening of the mounting hole 211 is rotated to face downward, and when the second connecting portion 21 moves upward relative to the rotating shaft 13, the mounting hole 211 can be separated from the rotating shaft 13 through the opening, so the staple 2 is separated from the cartridge 1.

Figure 3:
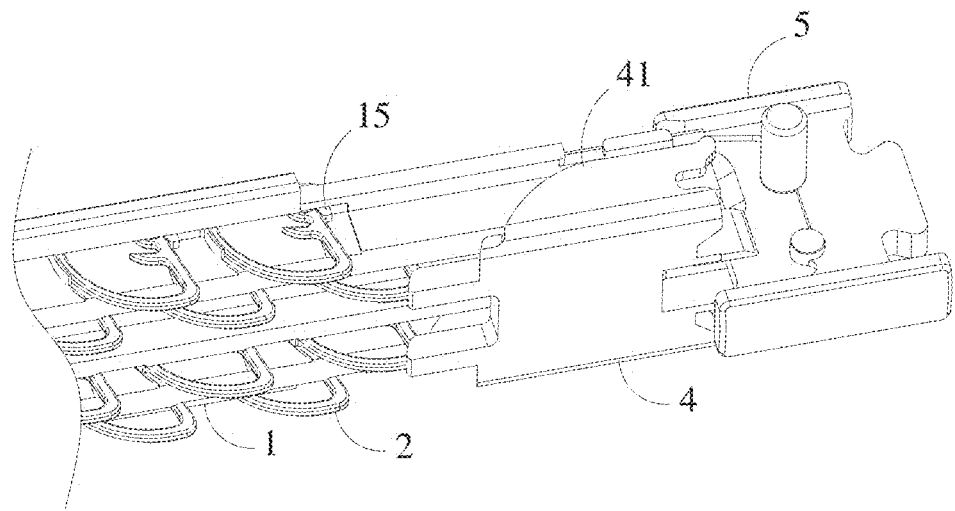
FIG. 3 is a perspective view of part of the cartridge assembly omitting the cartridge carrier and the cartridge cover according to the embodiment of the present disclosure.
Figure 8:
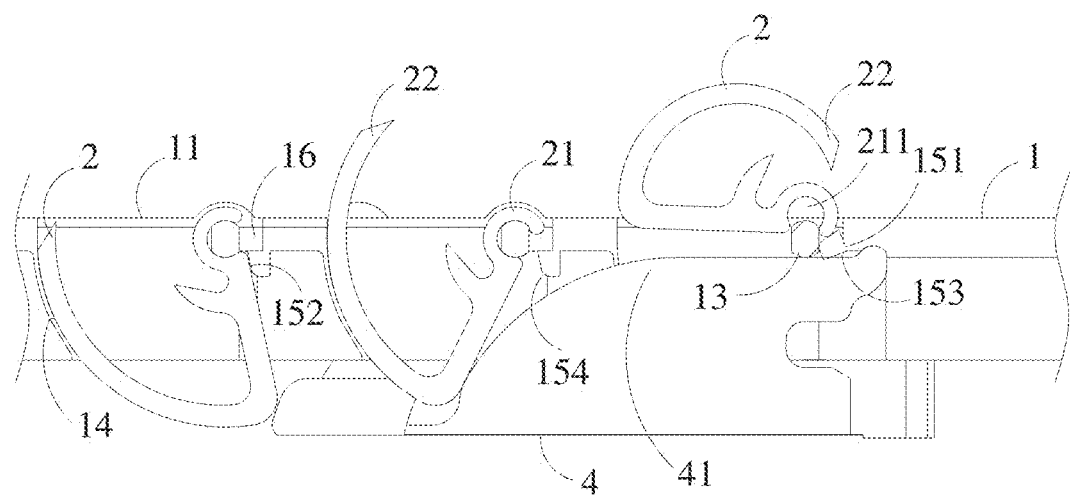
FIG. 8 is a schematic view of the staple mating portions cooperating with the staples when a staple is driven to rotate according to the embodiment of the present disclosure.

As shown in FIGS. 3, 4 and 8, the staple mating portion 15 is on a proximal side of the rotating shaft 13. A receiving space 16 is formed between the proximal side of the rotating shaft 13 and a distal surface 152 of the staple mating portion 15, After the staple mating portion 15 is driven by the actuation member 4 to rotate in the first direction, the staple mating portion 15 at least partially enters the receiving space 16. Furthermore, after the staple mating portion 15 rotates in the first direction and is located under the second connecting portion 21, the second connecting portion 21 can be lifted upward to separate the staple 2 from the staple cavity 12.

Figure 7:
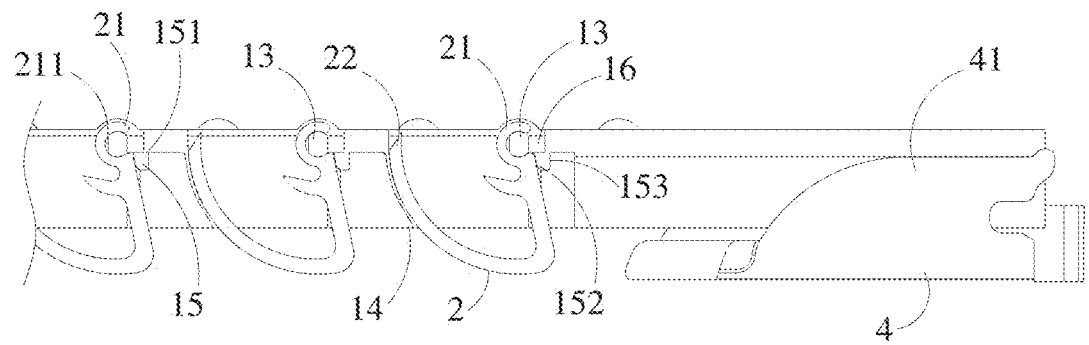
FIG. 7 is a schematic view of the staple mating portions cooperating with the staples when the staples are not driven according to the embodiment of the present disclosure.

FIGS. 5 to 8 only exemplarily show the staples 2 in the staple cavities 12 on an outermost side of the cartridge 1. In FIG. 7 and FIG. 8, section lines are omitted to clearly show the cooperation structures between various components. As shown in FIGS. 5 to 7, the staple mating portion 15 is rotatably connected to the proximal inner wall of the staple cavity 12 through the first connecting portion 151. In this embodiment, the staple mating portion 15 is integrally formed with the cartridge 1, and the staple mating portion 15 is connected to the proximal inner wall of the staple cavity 12 through weak link at a position of the first connecting portion 151. The weak link here means that when the staple mating portion 15 is not under external force, the staple mating portion 15 is connected to the inner wall of the staple cavity 12 through the first connecting portion 151 and maintains the initial state as shown in FIG. 7, when the staple mating portion 15 is driven by the actuation member 4 toward the distal side of the stapler, the staple mating portion 15 can rotate relative to the inner wall of the staple cavity 12 at the weak link of the first connecting portion 151, and the staple mating portion 15 remains connected with the cartridge 1. In other alternative embodiments, the staple mating portion 15 may be a component formed independently and rotatably connected to the inner wall of the staple cavity 12. In this embodiment, the distal surface 152 of the staple mating portion 15 is an inclined surface fitting a proximal surface of the staple 2, In an initial state, the distal surface 152 of the staple mating portion 15 abuts the proximal surface of the staple 2. In this embodiment, the proximal surface 153 of the staple mating portion 15 is a vertical surface fitting the distal surface of the staple driving portion 41. An upper surface of the staple mating portion 15 is a plane parallel to the cartridge surface 11. As shown in FIGS. 7 and 8, an arc-shaped guiding surface 154 is formed between a lower surface of the staple mating portion 15 and the distal surface 152 of the staple mating portion 15. When the staple mating portion 15 rotates in the first direction and at least partially enters the receiving space 16, the guiding surface 154 of the staple mating portion 15 cooperates with the side wall of the rotating shaft 13 to form a surface-to-surface fit, so interference between the rotating shaft 13 and the staple mating portion 15 is avoided, and point-to-face or point-to-point fit between the staple mating portion 15 and the rotating shaft 13 is also avoided.

As shown in FIGS. 5 to 7, the staple 2 further includes a staple leg 22. When the staple 2 is not under external force, the staple 2 is in an initial state. At this time, the second connecting portion 21 is on the proximal side of the staple cavity 12, and the staple leg 22 of the staple 2 is on the distal side of the staple cavity 12, and the staple leg 22 abuts an abutment surface 14 of the inner wall of the staple cavity 12. The actuation member 4 includes a staple driving portion 41. When the staple driving portion 41 is driven to move distally and contacts the staple 2, the staple 2 is driven to rotate around the rotating shaft 13 in the first direction by a first angle, and the staple leg 22 extends outward from the staple cavity 12 and contacts the anvil surface of the anvil, then the staple 2 is closed and formed under the action of the anvil. As shown in FIG. 8, after the staple 2 is driven by the actuation member 4 to rotate in the first direction by the first angle, the second connecting portion 21 and the staple leg 22 of the staple 2 are both located on the proximal side of the staple cavity 12, that is, the staple 2 enters a closed state.

As shown in FIG. 8, in this embodiment, a lowest point of the staple 2 is lower than that of the staple mating portion 15 in the height direction, and the distal surface of the staple driving portion 41 of the actuation member 4 is an inclined surface. When the actuation member 4 moves distally, the staple driving portion 41 first contacts the staple 2 and drives the staple 2 to rotate in the first direction. When the staple 2 rotates from the initial state in the first direction by the first angle, the staple leg 22 of the staple 2 extends outward from the cartridge surface 11 and is closed toward the proximal side under the action of the anvil surface, and the staple driving portion 41 of the actuation member 4 does not contact the staple mating portion 15. When the actuation member 4 continues to move distally after the staple 2 rotates by the first angle and, the staple driving portion 41 of the actuation member 4 contacts the staple mating portion 15 and drives the staple mating portion 15 to rotate in the first direction. The staple mating portion 15 acts on the proximal end of the second connecting portion 21 of the staple 2 to assist in driving the staple 2 to move upward. The second connecting portion 21 is separated from the rotating shaft 13 through the opening of the mounting hole 211, so the staple 2 is separated from the cartridge 1.

In this embodiment, the first angle refers to the rotation angle of the staple 2 corresponding to the staple driving portion 41 when the staple driving portion 41 first contacts the staple mating portion 15. The size of the first angle varies with the height of the staple mating portion 15. In the embodiment, when the lowest point of the staple mating portion 15 is at a lower height, the staple driving portion 41 will contact the staple mating portion 15 earlier, that is, the first angle is relatively small, and the staples 2 may not be completely closed after rotated by the angle. When the lowest point of the staple mating portion 15 is at a higher height, the staple driving portion 41 will contact the staple mating portion 15 later, that is, the first angle is relatively large, and the staples 2 may have been completely closed after rotated by the first angle.

In the embodiments shown in FIGS. 1 to 8, the first mating portion is the rotating shaft 13, and the second mating portion is the mounting hole 211. In another alternative embodiment, the first mating portion may be a groove provided on the inner wall of the staple cavity, an opening is provided on an upper side of the groove, and the opening of the groove is connected to the cartridge surface. The second mating portion is a rotating shaft located on at least one side of the second connecting portion, the rotating shaft at least partially enters the groove, and is rotatable relative to the groove. After the staple is closed and moves upward, the rotating shaft can be separated from the cartridge through the opening of the groove. The staple mating portion may be located on a proximal side of the groove, and drives the second connecting portion to move upward when the staple mating portion rotates in the first direction.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A cartridge assembly used for a surgical stapler, comprising:
a cartridge comprising a cartridge surface, wherein the cartridge surface is provided with a plurality of staple cavities, staple mating portions are provided on proximal sides of the staple cavities, each staple mating portion comprises a first connecting portion, and the staple mating portion is configured to be rotatably connected to a lower side of the cartridge surface through the first connecting portion;
a plurality of staples configured to be located in the staple cavities, wherein each staple comprises a second connecting portion, and the staple is configured to be rotatably connected to an inner wall of the staple cavity through the second connecting portion; each staple mating portion is on a proximal side of the second connecting portion of a corresponding staple; and
an actuation member configured to drive the staples and the staple mating portions to rotate in a first direction when the actuation member moves from a proximal side toward a distal side of the cartridge; wherein after each staple mating portion rotates, the second connecting portion of the corresponding staple is driven by the staple mating portion to move away from the cartridge and be separated from the staple cavity.

2. The cartridge assembly according to claim 1, wherein a first mating portion is provided on an inner wall of at least one side of the staple cavity, the second connecting portion of the staple is provided with a second mating portion, the second mating portion and the first mating portion are configured to form embedded cooperation, the second mating portion is rotatable and separable relative to the first mating portion, and the staple mating portion is on a proximal side of the first mating portion.

3. The cartridge assembly according to claim 2, wherein a receiving space is configured to be formed between the proximal side of the first mating portion and a distal surface of the staple mating portion; wherein after the staple mating portion is driven by the actuation member to rotate in the first direction, the staple mating portion at least partially enters the receiving space.

4. The cartridge assembly according to claim 1, wherein the staple mating portion is configured to be at least partially under the second connecting portion after the staple mating portion is rotated in the first direction.

5. The cartridge assembly according to claim 1, wherein a lowest point of the staple is lower than that of the staple mating portion in a height direction; when the actuation member moves distally, the actuation member first drives the staple to rotate in the first direction, and when the actuation member continues to move distally after the staple is rotated by a first angle, the actuation member drives the staple mating portion to rotate in the first direction.

6. The cartridge assembly according to claim 1, wherein the staple mating portion is configured to be integrally formed with the cartridge, and the staple mating portion is configured to be connected with the inner wall of the staple cavity through weak link at a position of the first connecting portion.

7. The cartridge assembly according to claim 1, wherein a distal surface of the staple mating portion is an inclined surface, and the distal surface of the staple mating portion is configured to abut the staple in an initial state.

8. The cartridge assembly according to claim 1, wherein after the actuation member drives the staple mating portion to rotate in the first direction, the staple mating portion remains connected with the cartridge.

9. The cartridge assembly according to claim 1, wherein a proximal surface of the staple mating portion is a vertical surface.

10. The cartridge assembly according to claim 1, wherein an upper surface of the staple mating portion is a plane parallel to an axial direction of the stapler, and/or, an arc-shaped guiding surface is provided between a lower surface of the staple mating portion and a distal surface of the staple mating portion.

11. A surgical stapler comprising the cartridge assembly according to claim 1.

* * * * *